United States Patent
Taneda

(10) Patent No.: US 10,612,062 B2
(45) Date of Patent: Apr. 7, 2020

(54) METHOD OF PRODUCING SACCHARIDES FROM BIOMASS WITH LESSER AMOUNT OF SACCHARIFYING ENZYME INEXPENSIVELY

(71) Applicant: JGC CORPORATION, Yokohama-shi, Kanagawa (JP)

(72) Inventor: Daisuke Taneda, Higashi Ibaraki-gun (JP)

(73) Assignee: JGC Corporation, Kanagawa (JP)

( * ) Notice: Subject to any disclaimer, the term of this patent is extended or adjusted under 35 U.S.C. 154(b) by 0 days.

(21) Appl. No.: 15/540,244

(22) PCT Filed: Jan. 30, 2015

(86) PCT No.: PCT/JP2015/052683
§ 371 (c)(1),
(2) Date: Jun. 27, 2017

(87) PCT Pub. No.: WO2016/121100
PCT Pub. Date: Aug. 4, 2016

(65) Prior Publication Data
US 2018/0002730 A1    Jan. 4, 2018

(51) Int. Cl.
 C12P 19/14       (2006.01)
 C12P 19/02       (2006.01)
 C13K 1/02        (2006.01)

(52) U.S. Cl.
CPC ............... *C12P 19/14* (2013.01); *C12P 19/02* (2013.01); *C13K 1/02* (2013.01); *C12P 2201/00* (2013.01); *C12P 2203/00* (2013.01)

(58) Field of Classification Search
None
See application file for complete search history.

(56) References Cited

U.S. PATENT DOCUMENTS

2015/0010959 A1* 1/2015 Taneda .................... C12P 19/14
435/99

FOREIGN PATENT DOCUMENTS

| JP | S55-156589 A | 12/1980 |
|---|---|---|
| JP | H01-175994 A | 7/1989 |
| JP | 2009-072144 A | 4/2009 |
| WO | WO 2005/024037 A2 | 3/2005 |
| WO | WO 2013/121551 A1 | 8/2013 |
| WO | WO2013121551 * | 8/2013 |

OTHER PUBLICATIONS

El-Diwany et al. Agricultural Wastes (1986), 18(2), 137-43. (Year: 1986).*
WO2013121551. Aug. 22, 2013. Machine translation. (Year: 2013).*
Kumar, R. and C.E. Wyman, "Effect of Additives on the Digestibility of Corn Stover Solids Following Pretreatment by Leading Technologies," Biotechnology and Bioengineering, 2009, 102(6), pp. 1544-1557.
International Search Report mailed by Japan Patent Office dated Apr. 21, 2015 in the corresponding PCT/JP2015/052683—4 pages.
Hori, Joji, "Alkaline Denaturation of Bovine Serum Albumin", Crystalline human serum albumin, Nutritional Biochemical Corp. (Control No. 5868), 24(2):69-72, 1980.

* cited by examiner

*Primary Examiner* — Christian L Fronda
(74) *Attorney, Agent, or Firm* — Knobbe, Martens, Olson & Bear, LLP

(57) ABSTRACT

A method of efficiently producing saccharides having glucose as the major component by inexpensively suppressing the non-productive adsorption of the enzyme to lignin is provided. The method of producing saccharides includes: a first step of preparing a water-soluble protein by adding at least any one of an animal protein and a vegetable protein to an aqueous sodium hydroxide solution or an aqueous calcium hydroxide solution to react with each other; a second step of adding the water-soluble protein to a slurry including a biomass; and a third step of producing saccharides having glucose as a major component by adding a degrading enzyme to the slurry for at least any one of a cellulose or a hemicellulose included in the biomass to be degraded by the degrading enzyme simultaneously with addition of the water-soluble protein to the slurry or after addition of the water-soluble protein.

7 Claims, 3 Drawing Sheets

METHOD OF PRODUCING SACCHARIDES FROM BIOMASS WITH LESSER AMOUNT OF SACCHARIFYING ENZYME INEXPENSIVELY

TECHNICAL FIELD

The present invention relates to a method of producing saccharides having glucose as the major component by enzymatically degrading at least any one of the cellulose or the hemicellulose included in the biomass.

BACKGROUND ART

The method of producing saccharides having glucose as the major component by using the cellulosic biomass (hereinafter, refereed as "the biomass", occasionally) as the raw material includes the enzymatic saccharification production technology, in which saccharides having glucose as the major component are produced by hydrolyzing at least any one of the cellulose and the hemicellulose (hereinafter, referred by "the cellulose and hemicellulose" or "the cellulose or the like", occasionally) by an enzyme.

Intrinsically, the enzyme (for example, a cellulase) added to the slurry including the biomass preferentially adsorbs to the lignin included in the biomass, rather than adsorbing to the cellulose or the like which is the material intended to be degraded, during enzymatically saccharifying the biomass in the enzymatic saccharification production technology. The enzyme that adsorbed to the lignin is not useful for degrading the cellulose or the like. Therefore, such adsorption is called as the non-productive adsorption. When the enzymes non-productively adsorb to the lignin, the amount of the enzyme functioning in degrading the cellulose or the like, which is the original intention, is reduced.

It is hard to recover the enzymes that adsorbed to the lignin. In addition, it is believed that the mechanism of adsorption of the enzyme to the lignin is based on the hydrophobic adsorption. If the adsorption of the enzyme to the lignin were based on the hydrophobic adsorption, the enzyme would adsorb to the lignin being deformed. Thus, it is believed that the enzyme have lost the originally retained activity. Since the enzyme is extremely expensive, there is a demand for the technology of suppressing the non-productive adsorption of the enzyme to the lignin.

Conventionally, it is known that the addition amount of the enzyme can be reduced by adding BSA (bovine serum albumin) or a surfactant in enzymatically saccharifying the biomass (for example, see Non Patent Literature 1 (NPL 1)).

RELATED ART DOCUMENTS

Non Patent Literature

NPL 1: Kumar, R. and C. E. Wyman, Effect of additives on the digestibility of corn stover solids following pretreatment by leading technologies. Biotechnol. Bioeng., 2009. 102(6): p. 1544-1557.

DISCLOSURE OF INVENTION

Problems to be Solved by the Present Invention

It is believed that the non-productive adsorption of the enzyme to the lignin is suppressed by BSA in the method disclosed in NPL 1. However, there is a problem that the cost of enzymatically saccharification is increased in the method since the unit prices of BSA and the surfactant are high. Therefore, there is a demand for the method of inexpensively suppressing the non-productive adsorption of the enzyme to the lignin.

The present invention is made under the circumstance described above. The purpose of the present invention is to provide a method of efficiently producing saccharides having glucose as the major component by inexpensively suppressing the non-productive adsorption of the enzyme to lignin is provided.

Means to Solving the Problems

An aspect of the present invention is a method of producing saccharides including:

a first step of preparing a water-soluble protein by adding at least any one of an animal protein and a vegetable protein to an aqueous sodium hydroxide solution or an aqueous calcium hydroxide solution to react with each other;

a second step of adding the water-soluble protein to a slurry including a biomass; and a third step of producing saccharides having glucose as a major component by adding a degrading enzyme to the slurry for at least any one of a cellulose or a hemicellulose included in the biomass to be degraded by the degrading enzyme simultaneously with addition of the water-soluble protein to the slurry or after addition of the water-soluble protein to the slurry.

In the method of producing saccharides of the present invention, a concentration of the aqueous sodium hydroxide solution or a concentration of the aqueous calcium hydroxide solution may be 0.05 mol/L to 1 mol/L.

In addition, in the case where the at least any one of an animal protein and a vegetable protein contains water, the final concentration of the aqueous sodium hydroxide solution or the final concentration of the aqueous calcium hydroxide solution after adding the at least any one of an animal protein and a vegetable protein may be 0.05 mol/L to 1 mol/L taking account of the amount of the water.

In the method of producing saccharides of the present invention, an addition amount of the at least any one of the animal protein and the vegetable protein (dry weight basis) with respect to the aqueous sodium hydroxide solution or the aqueous calcium hydroxide solution may be 1 mass % to 30 mass % of the aqueous sodium hydroxide solution or the aqueous calcium hydroxide solution.

In the method of producing saccharides of the present invention, a temperature of the reaction between: the aqueous sodium hydroxide solution or the aqueous calcium hydroxide solution; and the at least any one of the animal protein and the vegetable protein, in the first step may be 50° C. to 160° C.

In the method of producing saccharides of the present invention, a time of the reaction between: the aqueous sodium hydroxide solution or the aqueous calcium hydroxide solution; and the at least any one of the animal protein and the vegetable protein, in the first step may be 5 minutes to 90 minutes.

Effects of the Invention

According to the present invention, a method of efficiently producing saccharides having glucose as the major component by inexpensively suppressing the non-productive adsorption of the enzyme to lignin is provided.

EMBODIMENTS OF THE INVENTION

Figure 1:
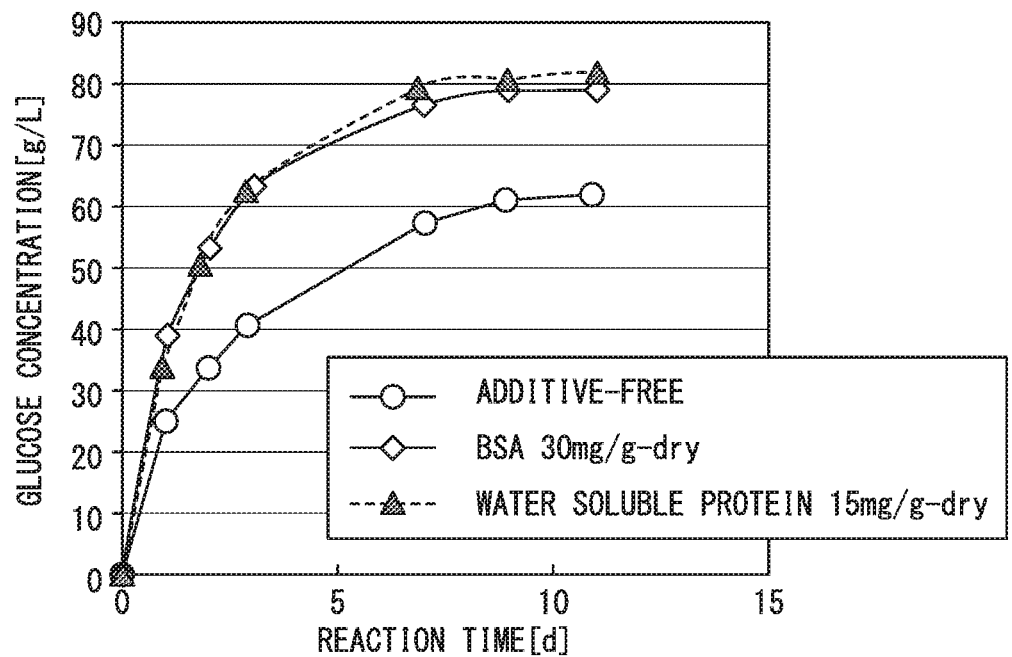
FIG. 1 is a graph showing the relationship between: the reaction time of enzymatic degradation; and the concentration of the produced glucose in Example 1 of the present invention; and Comparative Examples 1 and 2.

Embodiment of the method of producing saccharides, which is an aspect of the present invention, is explained below.

The embodiments of the present invention are for only specifically explaining for better understanding of the scope of the present invention, and are not for limiting the present invention unless otherwise noted.

[Method of Producing Saccharides]

The method of producing saccharides of the present embodiment includes the first, second and third steps described below.

First, the water-soluble protein is prepared by adding at least any one of an animal protein and a vegetable protein to an aqueous sodium hydroxide solution or an aqueous calcium hydroxide solution to react with each other in the first step.

The water-soluble protein is added to slurry including a biomass in the second step.

Saccharides having glucose as a major component are produced in the third step by adding a degrading enzyme to the slurry for at least any one of a cellulose or a hemicellulose included in the biomass to be degraded by the degrading enzyme. The addition of the degrading enzyme to the slurry is performed simultaneously with addition of the water-soluble protein to the slurry or after addition of the water-soluble protein to the slurry.

A pre-treatment is performed to the biomass (woods, weeds, or crop residues) in the method of producing saccharides of the present embodiment. Contact efficiency between: at least any one of cellulose and hemicellulose included in the biomass; and the degrading enzyme of at least any one of cellulose and hemicellulose, is improved by performing the pre-treatment.

The pre-treatment includes the alkali treatment, the organic solvent treatment, the dilute sulfuric acid treatment, the steam blasting treatment and the like to the biomass. However, from the standpoint of the enzymatic saccharification yield and equipment costs, the steam blasting treatment, the alkali treatment or the dilute sulfuric acid treatment can be suitably utilized.

As the alkali treatment, the organic solvent treatment, the dilute sulfuric acid treatment, and the steam blasting treatment to the biomass, the known treatments can be utilized.

Next, the slurry including biomass (hereinafter, referred as "the biomass slurry" occasionally) is prepared by dispersing the pre-treated biomass in a solution (solvent).

The concentration of the biomass slurry, which is the concentration of the biomass in the biomass slurry, is appropriately adjusted depending on the kind of the biomass, the pre-treatment method or the like. However, preferably it is 10 g-dry to 30 g-dry to 100 mL of the solution.

As the solution (solvent) used for preparing the biomass slurry, water can be named, for example.

As long as the content of the biomass in the biomass slurry is within the above-described range, a moderate amount of the free solution exists without being absorbed entirely in the fine pores of the biomass. Thus, the degrading enzyme can move freely in the biomass slurry. In addition, reactivity between the degrading enzyme and at least any one of cellulose and hemicellulose is improved, since stirring operation of the biomass becomes easy. In addition, if the concentration of the biomass slurry were less than 10 w/v %, the production efficiency of saccharides having glucose as the major component would be deteriorated to an unacceptable level. Therefore, it is not preferable.

In addition, at least any one of an animal protein and a vegetable protein is added to the aqueous sodium hydroxide solution or the aqueous calcium hydroxide solution apart from the above-described pretreatment in the method of producing saccharides of the present embodiment. Because of this, the aqueous sodium hydroxide solution or the aqueous calcium hydroxide solution; and the at least any one of an animal protein and a vegetable protein, are reacted with each other for the water-soluble protein to be prepared (the first step).

The at least any one of an animal protein and a vegetable protein means: any one of the animal protein and the vegetable protein; or both of the animal protein and the vegetable protein.

The aqueous sodium hydroxide solution or the aqueous calcium hydroxide solution; and the at least any one of an animal protein and a vegetable protein reacting with each other means that having the aqueous sodium hydroxide solution or the aqueous calcium hydroxide solution; and the at least any one of an animal protein and a vegetable protein, contacts each other.

More specifically, the aqueous sodium hydroxide solution or the aqueous calcium hydroxide solution; and the at least any one of an animal protein and a vegetable protein, are fed in a reaction tank in the first step. Then, the aqueous sodium hydroxide solution or the aqueous calcium hydroxide solution; and the at least any one of an animal protein and a vegetable protein, are mixed to obtain the mixed solution. Next, the mixed solution is retained (heated) at a predetermined reaction temperature; and the heated mixed solution is stirred for a predetermined time. After that, heating of the mixed solution is stopped; and the mixed solution is withdrawn from the reaction tank to be filtered. Next, pH of the filtered solution is adjusted to 4-6.

Alternatively, the aqueous sodium hydroxide solution or the aqueous calcium hydroxide solution; and the at least any one of an animal protein and a vegetable protein, are fed in a reaction tank in the first step. Then, the aqueous sodium hydroxide solution or the aqueous calcium hydroxide solution; and the at least any one of an animal protein and a vegetable protein, are mixed to obtain the mixed solution. Next, the mixed solution is retained (heated) at a predetermined reaction temperature; and the heated mixed solution is stirred for a predetermined time. Next, heating of the mixed solution is stopped and pH of the mixed solution is adjusted to 4-6.

The reaction temperature (the temperature of the reaction) means the temperature of the mixed solution of: the aqueous sodium hydroxide solution or the aqueous calcium hydroxide solution; and the at least any one of an animal protein and a vegetable protein in contacting the aqueous sodium hydroxide solution or the aqueous calcium hydroxide solution to the at least any one of an animal protein and a vegetable protein. When the temperature of the mixed solution has not reached to the temperature (the reaction temperature) described below, it is regarded that the mixed solution has not retained at the reaction temperature.

The animal proteins include: yeast; cell bodies of a filamentous fungi or the like; internal organs of livestock; skins of livestock; and the like. In the present specification, even yeast and cell bodies of a filamentous fungi or the like are regarded as the animal proteins.

The vegetable proteins include: the distillation residue generated from a food-based ethanol plant; proteins of cereals generated from the starch factory, the grinding factory, the rice mill factory, or the like. Cereal proteins include the rice bran, the wheat bran, and the like.

It is preferable that the concentration of the aqueous sodium hydroxide or the aqueous calcium hydroxide, which is the amount of sodium hydroxide included in the aqueous sodium hydroxide (content) or the amount of calcium hydroxide included in the aqueous calcium hydroxide (content), is 0.05 mol/L to 1 mol/L. More preferably, each of the contents is 0.1 mol/L to 0.5 mol/L. In addition, in the case where the at least any one of an animal protein and a vegetable protein contains water, the final concentration of the aqueous sodium hydroxide solution or the final concentration of the aqueous calcium hydroxide solution after adding the at least any one of an animal protein and a vegetable protein is 0.05 mol/L to 1 mol/L taking account of the amount of the water.

If the concentration of the aqueous sodium hydroxide or the aqueous calcium hydroxide were less than 0.05 mol/L, reaction between these aqueous solutions with the animal or vegetable proteins would become insufficient for the produce amount of the intended water-soluble protein to be reduced. On the other hand, if the concentration of the aqueous sodium hydroxide or the aqueous calcium hydroxide exceeded 1 mol/L, the animal proteins and the vegetable proteins would excessively degraded for the quality of the water-soluble protein as the non-productive adsorption inhibitor to be deteriorated.

By adding acid to the above-described filtered solution or the mixed solution including the water-soluble protein obtained by reacting the aqueous sodium hydroxide solution or the aqueous calcium hydroxide solution with the at least any one of an animal protein and a vegetable protein, pH of the solutions are adjusted. It is preferable that pH is 4-6. More preferably, it is 5.

If pH of the above-described filtered solution or pH of the above-described mixed solution were less than 4 or exceeded 6, the saccharifying activity of the enzyme degrading at least any one of the cellulose and the hemicellulose included in the biomass would be inhibited.

It is preferable that the addition amount of the at least any one of the animal protein and the vegetable protein (dry weight basis) with respect to the aqueous sodium hydroxide solution or the aqueous calcium hydroxide solution is 1 mass % to 30 mass % of the aqueous sodium hydroxide solution or the aqueous calcium hydroxide solution. More preferably, it is 5 mass % to 20 mass %.

If the addition amount of the at least any one of the animal protein and the vegetable protein were less than 1 mass %, the produce amount of the intended water-soluble protein would be reduced. If the addition amount of the at least any one of the animal protein and the vegetable protein exceeded 30 mass %, the animal proteins and the vegetable proteins would excessively degraded for the quality of the water-soluble protein as the non-productive adsorption inhibitor to be deteriorated.

It is preferable that the temperature of the reaction between: the aqueous sodium hydroxide solution or the aqueous calcium hydroxide solution; and the at least any one of the animal protein and the vegetable protein, in the first step is 50° C. to 160° C. More preferably, it is 70° C. to 100° C.

If the temperature of the reaction between: the aqueous sodium hydroxide solution or the aqueous calcium hydroxide solution; and the at least any one of the animal protein and the vegetable protein, were less than 50° C., the reaction between the aqueous sodium hydroxide solution or the aqueous calcium hydroxide solution; and the at least any one of the animal protein and the vegetable protein would become insufficient for the produce amount of the intended water-soluble protein to be reduced. On the other hand, if the temperature of the reaction between: the aqueous sodium hydroxide solution or the aqueous calcium hydroxide solution; and the at least any one of the animal protein and the vegetable protein, exceeded 160° C., the animal proteins and the vegetable proteins would excessively degraded for the quality of the water-soluble protein as the non-productive adsorption inhibitor to be deteriorated.

The reaction between: the aqueous sodium hydroxide solution or the aqueous calcium hydroxide solution; and the at least any one of the animal protein and the vegetable protein, in the first step is the reaction, in which the water-soluble protein having the low molecular weight molecular structure ionized easily are produced by hydrolyzing the at least any one of the animal protein and the vegetable protein by the aqueous sodium hydroxide solution or the aqueous calcium hydroxide solution.

It is preferable that the time of the reaction between: the aqueous sodium hydroxide solution or the aqueous calcium hydroxide solution; and the at least any one of the animal protein and the vegetable protein, in the first step is 5 minutes to 90 minutes. More preferably, it is 10 minutes to 60 minutes.

If the time of the reaction between: the aqueous sodium hydroxide solution or the aqueous calcium hydroxide solution; and the at least any one of the animal protein and the vegetable protein, were less than 5 minutes, the reaction between the aqueous sodium hydroxide solution or the aqueous calcium hydroxide solution; and the animal protein and the vegetable protein would become insufficient for the produce amount of the intended water-soluble protein to be reduced. On the other hand, if the time of the reaction between: the aqueous sodium hydroxide solution or the aqueous calcium hydroxide solution; and the at least any one of the animal protein and the vegetable protein, exceeded 90 minutes, the animal proteins and the vegetable proteins would excessively degraded for the quality of the water-soluble protein as the non-productive adsorption inhibitor to be deteriorated.

The reaction time (the time of the reaction) means the time, in which the mixed solution of: the aqueous sodium hydroxide solution or the aqueous calcium hydroxide solution; and the at least any one of the animal protein and the vegetable protein is retained at a predetermined temperature and stirred in the reaction tank. Thus, when the temperature of the mixed solution has not reached to the above-described temperature (the reaction temperature), the period is not included in the reaction time of the mixed solution.

Next, the biomass slurry and the water-soluble protein is mixed by adding the water-soluble protein prepared in the above-described first step to the above-described biomass slurry (the second step).

It is preferable that the addition amount of the water-soluble protein with respect to the biomass slurry is 5 mg/g-dry to 40 mg/g-dry per 1 g of the dried biomass. More preferably, it is 5 mg/g-dry to 20 mg/g-dry.

If the addition amount of the water-soluble protein were less than 5 mg/g-dry, the effect of suppressing adsorption of the degrading enzyme to the lignin contained in the biomass slurry would not be obtained sufficiently during adding the enzyme degrading the at least any one of the cellulose and the hemicellulose to the biomass slurry. On the other hand, if the additional amount of the water-soluble protein exceeded 40 mg/g-dry, the addition amount of the water-soluble protein would be excessive for the production cost to be increased.

In addition, the stirring blades or the like is used for mixing the biomass slurry and the water-soluble protein.

Next, the mixture of the above-described biomass slurry and the water-soluble protein; and the solution including an appropriate amount of the degrading enzyme (the enzyme solution), which is suited for degrading at least any one of the cellulose and the hemicellulose included in the mixture, are mixed (the third step). In other words, the degrading enzyme is added to the biomass slurry after adding the water-soluble protein to the biomass slurry. Alternatively, the water-soluble protein and the solution including the appropriate amount of the degrading enzyme are added to the biomass slurry simultaneously (the third step).

In the third step, pH of the reaction tank solution is adjusted in such a way that pH of the reaction tank solution, which includes: the mixture of the biomass slurry and the water-soluble protein; and the degrading enzyme solution, becomes the most suitable pH condition for the degrading enzyme used. In addition, the temperature of the reaction tank is adjusted in such a way that the temperature becomes the most suitable temperature for the used degrading enzyme.

In the third step, it is preferable that pH of the reaction tank solution is adjusted for the degrading enzyme to function actively. Specifically, it is preferable that pH is adjusted to 4 to 6.

In addition, it is preferable that the temperature of the reaction tank solution is adjusted for the degrading enzyme to function actively in the third step. Specifically, it is preferable that the temperature of the reaction tank solution is adjusted to 40° C. to 60° C.

As the degrading enzyme for degrading the biomass, a cellulase is used, for example. In the case where hemicellulose is included in the biomass, it is preferable that a xylanase or a mannanase is added in addition to the cellulase as the enzyme degrading the hemicellulose.

For stirring the reaction tank solution, stirring blades or the like are used.

By stirring and mixing the reaction tank solution gently enough not to excessively deactivate the degrading enzyme included in the in the reaction tank, the biomass (at least any one of cellulose and hemicellulose) is enzymatically saccharified efficiently in the present embodiment (the enzymatically saccharifying reaction step).

In addition, in this enzymatically saccharifying reaction step, it is preferable that the temperature of the reaction tank solution is adjusted for the enzyme to function actively. Specifically, it is preferable that the temperature of the reaction tank solution is retained to 40° C. to 60° C.

The enzymatically saccharifying reaction step is performed: to the point where the saccharification of the biomass by the degrading enzyme proceeds sufficiently and until there is no progression of the reaction further; or until the final reaction rate becomes 80% or more. For example, the enzymatic degradation of the biomass is performed for 2 days to 10 days at 40° C. to 60° C.

In the method of producing saccharides of the present embodiment, the water-soluble protein is prepared by adding the at least any one of the animal protein and the vegetable protein to the aqueous sodium hydroxide solution the aqueous calcium hydroxide solution to react with each other. Then, by adding the water-soluble protein to the biomass slurry and by adding the degrading enzyme, the at least any one of the cellulose and the hemicellulose is degraded by the degrading enzyme. The addition of the degrading enzyme to the biomass slurry is performed: simultaneously with the addition of the water-soluble protein to the biomass slurry; or after the addition of the water-soluble protein to the biomass slurry.

The water-soluble protein is capable of suppressing the non-productive adsorption of the degrading enzyme to the lignin included in the biomass slurry. Thus, the usage of the enzyme in the enzymatic saccharification reaction step can be reduced than before. In addition, the addition amount of the water-soluble protein for obtaining the equal amount of saccharides having glucose as the major component can be reduced compared to the conventional method using the bovine serum albumin (BSA), the protein derived from cheese whey, or the like as the additive preventing the non-productive adsorption of the degrading enzyme to the lignin. Furthermore, in the case where the addition amount of the conventional additive and the addition amount of the water-soluble protein in the present embodiment are the same, more saccharides having glucose as the major component can be obtained in the method of producing saccharides of the present embodiment than the conventional methods.

In addition: yeast; cell bodies of a filamentous fungi or the like; internal organs of livestock; skins of livestock; the distillation residue generated from a food-based ethanol plant; proteins of cereals generated from the starch factory, the grinding factory, the rice mill factory, or the like; or the like, is used as the animal protein and the vegetable protein, which become raw materials of the water-soluble protein. Therefore, the cost can be reduced as compared with the case of using the bovine serum albumin (BSA), the protein derived cheese whey, or the like, which is conventionally used as the additive preventing the non-productive adsorption of the degrading enzyme to the lignin.

EXAMPLES

The present invention is explained in more detail by Examples of the present invention and Comparative Examples below. However, the present invention is not limited by the descriptions of Examples below.

Example 1

The slurry including the bagasse was prepared by dispersing 10 g of the bagasse treated with steam blasting in 50 mL of water. The content of the bagasse in the obtained slurry was 20 w/v %.

In addition, the water-soluble protein was prepared by adding the rice bran to the aqueous sodium hydroxide solution for the aqueous sodium hydroxide solution and the rice bran to react with each other.

At this time, the concentration of the aqueous sodium hydroxide solution was set to 0.5 mol/L. In addition, the addition amount of the rice bran with respect to the aqueous sodium hydroxide solution was set to 10 mass % of the aqueous sodium hydroxide solution.

In addition, the reaction temperature and the reaction time between the aqueous sodium hydroxide solution and the rice bran were set to 75° C. and 10 minutes, respectively.

Next, the aqueous sodium hydroxide solution including the water-soluble protein was filtered; and pH of the filtered aqueous sodium hydroxide solution including the water-soluble protein was adjusted to 5.

Next, the cellulase and the aqueous sodium hydroxide solution were added to the biomass slurry to be mixed with each other.

At this time, the addition amount of the water-soluble protein with respect to the biomass slurry was set to 15 mg/g-dry per 1 g of the dried biomass. In addition, the addition amount of the cellulase with respect to the biomass slurry was set to 5 mg/g-dry per 1 g of the dried biomass.

The operation condition is summarized below.
Bagasse mass: 10 g-dry
Addition amount of the water-soluble protein: 15 mg/g-substrate
Addition amount of the cellulase: 4 mg/g-substrate
Solution amount: 50 mL
Temperature: 50° C.
pH: 5

The relationship between: the reaction time for the enzymatic degradation (day); and the glucose concentration in the solution (g/L) was investigated. The results are shown in FIG. 1.

In addition, the concentrations of the finally obtained glucose (g/L) were measured. The results are shown in FIGS. 2-5.

Comparative Example 1

Except for not adding the water-soluble protein to the biomass slurry, the bagasse included in the biomass slurry was degraded by the cellulase as in Example 1.

In addition, as in Example 1, the relationship between: the reaction time for the enzymatic degradation (day); and the glucose concentration in the solution (g/L) was investigated. The results are shown in FIG. 1.

Comparative Example 2

Except for adding the bovine serum albumin instead of the water-soluble protein to the biomass slurry, the bagasse included in the biomass slurry was degraded by the cellulase as in Example 1.

The addition amount of the bovine serum albumin with respect to the biomass slurry was set to 30 mg/g-dry per 1 g of the dried biomass.

In addition, as in Example 1, the relationship between: the reaction time for the enzymatic degradation (day); and the glucose concentration in the solution (g/L) was investigated. The results are shown in FIG. 1.

Based on the results shown in FIG. 1, it was demonstrated that the glucose concentrations in the solutions were increased by about 20 g/L in the case where: the water-soluble protein was added to the biomass slurry as in Example 1 of the present invention; or the bovine serum albumin was added as in Example 2 of the present invention, compared to Comparative Example 1 without an additive.

In addition, it was demonstrated that, when the water-soluble protein was used, the equivalent effect could be obtained with ½ of the addition amount of the bovine serum albumin with respect to the biomass slurry.

Example 2

Except for setting the reaction time between sodium hydroxide and the rice bran to 5 minutes, the water-soluble protein was prepared as in Example 1 of the present invention.

Figure 2:
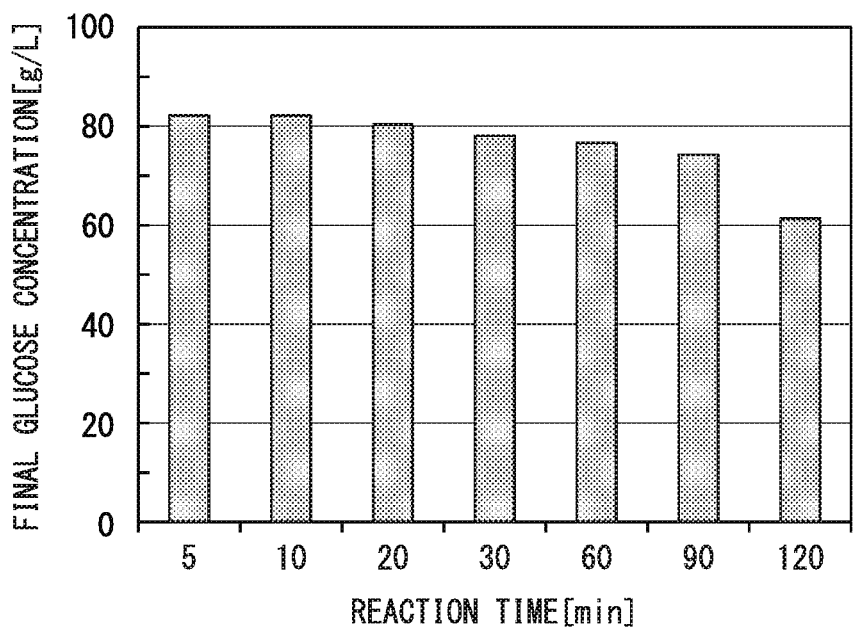
FIG. 2 is a graph showing the relationship between: the reaction time between sodium hydroxide and the rice bran; and the final concentration of the obtained glucose in Examples 1-6 of the present invention; and Comparative Example 3.

The enzymatic degradation reaction was performed as in Example 1 of the present invention. The concentration of the finally obtained glucose (g/L) was measured. The results are shown in FIG. 2.

Example 3

Except for setting the reaction time between sodium hydroxide and the rice bran to 20 minutes, the water-soluble protein was prepared as in Example 1 of the present invention.

The enzymatic degradation reaction was performed as in Example 1 of the present invention. The concentration of the finally obtained glucose (g/L) was measured. The results are shown in FIG. 2.

Example 4

Except for setting the reaction time between sodium hydroxide and the rice bran to 30 minutes, the water-soluble protein was prepared as in Example 1 of the present invention.

The enzymatic degradation reaction was performed as in Example 1 of the present invention. The concentration of the finally obtained glucose (g/L) was measured. The results are shown in FIG. 2.

Example 5

Except for setting the reaction time between sodium hydroxide and the rice bran to 60 minutes, the water-soluble protein was prepared as in Example 1 of the present invention.

The enzymatic degradation reaction was performed as in Example 1 of the present invention. The concentration of the finally obtained glucose (g/L) was measured. The results are shown in FIG. 2.

Example 6

Except for setting the reaction time between sodium hydroxide and the rice bran to 90 minutes, the water-soluble protein was prepared as in Example 1 of the present invention.

The enzymatic degradation reaction was performed as in Example 1 of the present invention. The concentration of the finally obtained glucose (g/L) was measured. The results are shown in FIG. 2.

Comparative Example 3

Except for setting the reaction time between sodium hydroxide and the rice bran to 120 minutes, the water-soluble protein was prepared as in Example 1 of the present invention.

The enzymatic degradation reaction was performed as in Example 1 of the present invention. The concentration of the finally obtained glucose (g/L) was measured. The results are shown in FIG. 2.

Based on the results shown in FIG. 2, it was demonstrated that the concentrations of the finally obtained glucose were higher in the cases where the reaction time between sodium hydroxide and the rice bran was set to 5 minutes to 90 minutes as in Examples 1 to 6 of the present invention than in the case where the reaction time between sodium hydroxide and the rice bran was set to 120 minutes as in Comparative Example 3.

Example 7

Except for setting the concentration of the aqueous sodium hydroxide solution to 0.05 mol/L, the water-soluble protein was prepared as in Example 1 of the present invention.

Figure 3:
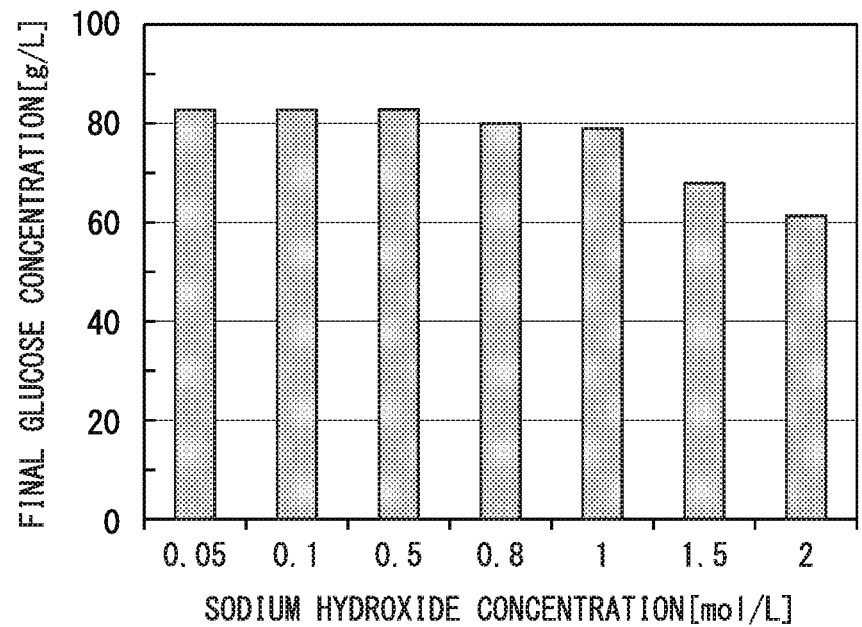
FIG. 3 is a graph showing the relationship between; the concentration of the aqueous sodium hydroxide solution; and the final concentration of the obtained glucose in Examples 1, 7-10 of the present invention; and Comparative Examples 4 and 5.

The enzymatic degradation reaction was performed as in Example 1 of the present invention. The concentration of the finally obtained glucose (g/L) was measured. The results are shown in FIG. 3.

Example 8

Except for setting the concentration of the aqueous sodium hydroxide solution to 0.1 mol/L, the water-soluble protein was prepared as in Example 1 of the present invention.

The enzymatic degradation reaction was performed as in Example 1 of the present invention. The concentration of the finally obtained glucose (g/L) was measured. The results are shown in FIG. 3.

Example 9

Except for setting the concentration of the aqueous sodium hydroxide solution to 0.8 mol/L, the water-soluble protein was prepared as in Example 1 of the present invention.

The enzymatic degradation reaction was performed as in Example 1 of the present invention. The concentration of the finally obtained glucose (g/L) was measured. The results are shown in FIG. 3.

Example 10

Except for setting the concentration of the aqueous sodium hydroxide solution to 1 mol/L, the water-soluble protein was prepared as in Example 1 of the present invention.

The enzymatic degradation reaction was performed as in Example 1 of the present invention. The concentration of the finally obtained glucose (g/L) was measured. The results are shown in FIG. 3.

Comparative Example 4

Except for setting the concentration of the aqueous sodium hydroxide solution to 1.5 mol/L, the water-soluble protein was prepared as in Example 1 of the present invention.

The enzymatic degradation reaction was performed as in Example 1 of the present invention. The concentration of the finally obtained glucose (g/L) was measured. The results are shown in FIG. 3.

Comparative Example 5

Except for setting the concentration of the aqueous sodium hydroxide solution to 2 mol/L, the water-soluble protein was prepared as in Example 1 of the present invention.

The enzymatic degradation reaction was performed as in Example 1 of the present invention. The concentration of the finally obtained glucose (g/L) was measured. The results are shown in FIG. 3.

Based on the results shown in FIG. 3, it was demonstrated that the concentrations of the finally obtained glucose were higher in the cases where the concentration of the aqueous sodium hydroxide solution was set to 0.05 mol/L to 1 mol/L as in Example 1 and Examples 7 to 6 of the present invention than in the cases where the concentration of the aqueous sodium hydroxide solution was set to 1.5 mol/L to 2 mol/L as in Comparative Examples 4 and 5.

Example 11

Except for setting the addition amount of the rice bran with respect to the aqueous sodium hydroxide to 1 mass % of the aqueous sodium hydroxide solution, the water-soluble protein was prepared as in Example 1 of the present invention.

Figure 4:
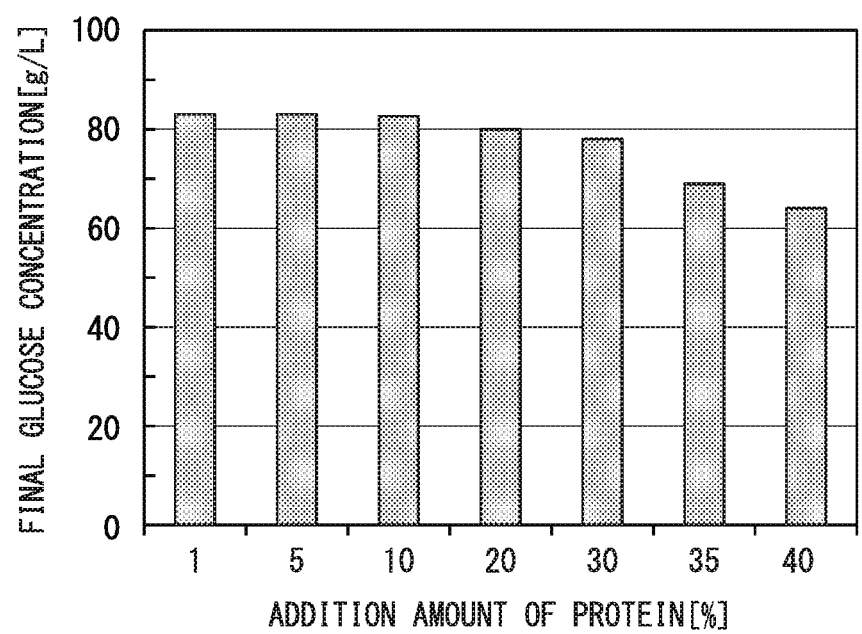
FIG. 4 is a graph showing the relationship between: the addition amount of the rice bran with respect to the aqueous sodium hydroxide solution; and the final concentration of the obtained glucose in Examples 1, 11-14 of the present invention; and Comparative Examples 6 and 7.

The enzymatic degradation reaction was performed as in Example 1 of the present invention. The concentration of the finally obtained glucose (g/L) was measured. The results are shown in FIG. 4.

Example 12

Except for setting the addition amount of the rice bran with respect to the aqueous sodium hydroxide to 5 mass % of the aqueous sodium hydroxide solution, the water-soluble protein was prepared as in Example 1 of the present invention.

The enzymatic degradation reaction was performed as in Example 1 of the present invention. The concentration of the finally obtained glucose (g/L) was measured. The results are shown in FIG. 4.

Example 13

Except for setting the addition amount of the rice bran with respect to the aqueous sodium hydroxide to 20 mass % of the aqueous sodium hydroxide solution, the water-soluble protein was prepared as in Example 1 of the present invention.

The enzymatic degradation reaction was performed as in Example 1 of the present invention. The concentration of the finally obtained glucose (g/L) was measured. The results are shown in FIG. 4.

Example 14

Except for setting the addition amount of the rice bran with respect to the aqueous sodium hydroxide to 30 mass % of the aqueous sodium hydroxide solution, the water-soluble protein was prepared as in Example 1 of the present invention.

The enzymatic degradation reaction was performed as in Example 1 of the present invention. The concentration of the finally obtained glucose (g/L) was measured. The results are shown in FIG. 4.

Comparative Example 6

Except for setting the addition amount of the rice bran with respect to the aqueous sodium hydroxide to 35 mass % of the aqueous sodium hydroxide solution, the water-soluble protein was prepared as in Example 1 of the present invention.

The enzymatic degradation reaction was performed as in Example 1 of the present invention. The concentration of the finally obtained glucose (g/L) was measured. The results are shown in FIG. 4.

Comparative Example 7

Except for setting the addition amount of the rice bran with respect to the aqueous sodium hydroxide to 40 mass % of the aqueous sodium hydroxide solution, the water-soluble protein was prepared as in Example 1 of the present invention.

The enzymatic degradation reaction was performed as in Example 1 of the present invention. The concentration of the finally obtained glucose (g/L) was measured. The results are shown in FIG. 4.

Based on the results shown in FIG. 4, it was demonstrated that the concentrations of the finally obtained glucose were higher in the cases where the addition amount of the rice bran with respect to the aqueous sodium hydroxide solution was set to 1 mass % to 30 mass % of the aqueous sodium hydroxide solution as in Example 1 and Examples 11 to 14 of the present invention than in the cases where the addition amount of the rice bran was set to 35 mass % to 40 mass % of the aqueous sodium hydroxide solution as in Comparative Examples 6 and 7.

Example 15

Except for setting the reaction temperature between sodium hydroxide and the rice bran to 50° C., the water-soluble protein was prepared as in Example 1 of the present invention.

Figure 5:
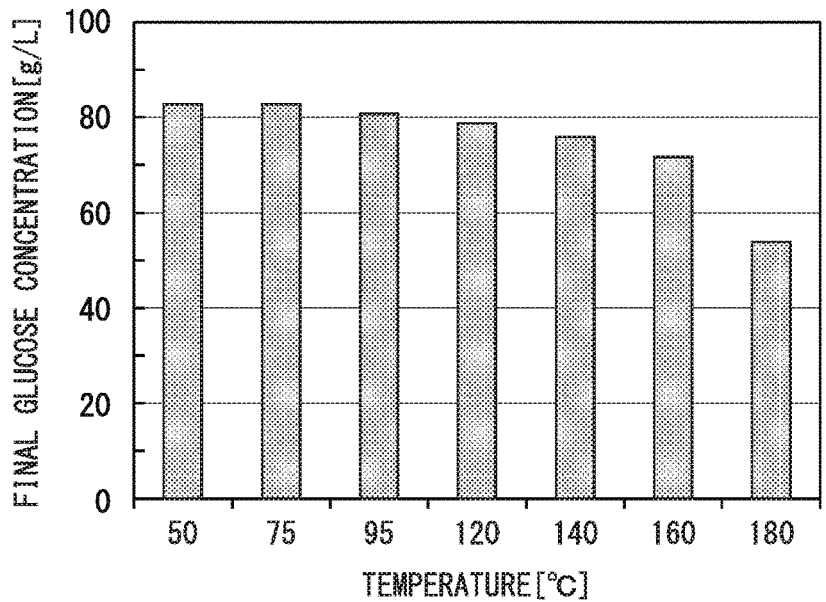
FIG. 5 is a graph showing the relationship between: the reaction temperature between the aqueous sodium hydroxide solution and the rice bran; and the final concentration of the obtained glucose in Examples 1, 15-19 of the present invention; and Comparative Example 8.

The enzymatic degradation reaction was performed as in Example 1 of the present invention. The concentration of the finally obtained glucose (g/L) was measured. The results are shown in FIG. 5.

Example 16

Except for setting the reaction temperature between sodium hydroxide and the rice bran to 95° C., the water-soluble protein was prepared as in Example 1 of the present invention.

The enzymatic degradation reaction was performed as in Example 1 of the present invention. The concentration of the finally obtained glucose (g/L) was measured. The results are shown in FIG. 5.

Example 17

Except for setting the reaction temperature between sodium hydroxide and the rice bran to 120° C., the water-soluble protein was prepared as in Example 1 of the present invention.

The enzymatic degradation reaction was performed as in Example 1 of the present invention. The concentration of the finally obtained glucose (g/L) was measured. The results are shown in FIG. 5.

Example 18

Except for setting the reaction temperature between sodium hydroxide and the rice bran to 140° C., the water-soluble protein was prepared as in Example 1 of the present invention.

The enzymatic degradation reaction was performed as in Example 1 of the present invention. The concentration of the finally obtained glucose (g/L) was measured. The results are shown in FIG. 5.

Example 19

Except for setting the reaction temperature between sodium hydroxide and the rice bran to 160° C., the water-soluble protein was prepared as in Example 1 of the present invention.

The enzymatic degradation reaction was performed as in Example 1 of the present invention. The concentration of the finally obtained glucose (g/L) was measured. The results are shown in FIG. 5.

Comparative Example 8

Except for setting the reaction temperature between sodium hydroxide and the rice bran to 180° C., the water-soluble protein was prepared as in Example 1 of the present invention.

The enzymatic degradation reaction was performed as in Example 1 of the present invention. The concentration of the finally obtained glucose (g/L) was measured. The results are shown in FIG. 5.

Based on the results shown in FIG. 5, it was demonstrated that the concentrations of the finally obtained glucose were higher in the cases where the reaction temperature between hydroxide and the rice bran was set to 50° C. to 160° C. as in Example 1 and Examples 15 to 19 of the present invention than in the case where the reaction temperature between hydroxide and the rice bran was set to 180° C. as in Comparative Example 8.

Example 20

Except for using yeast instead of the rice bran, the water-soluble protein was prepared as in Example 1 of the present invention.

Figure 6:
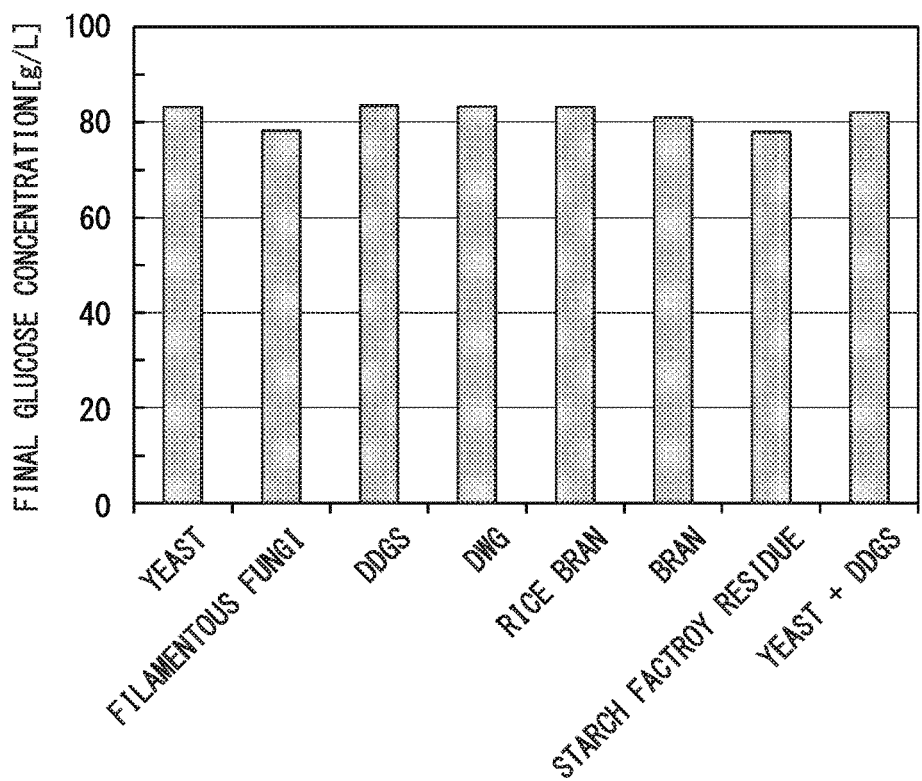
FIG. 6 is a graph showing the relationship between: the kinds of the water-soluble protein; and the final concentration of the obtained glucose in Examples 1, 20-26 of the present invention.

The enzymatic degradation reaction was performed as in Example 1 of the present invention. The concentration of the finally obtained glucose (g/L) was measured. The results are shown in FIG. 6.

Example 21

Except for using the filamentous fungi instead of the rice bran, the water-soluble protein was prepared as in Example 1 of the present invention.

The enzymatic degradation reaction was performed as in Example 1 of the present invention. The concentration of the finally obtained glucose (g/L) was measured. The results are shown in FIG. 6.

Example 22

Except for using DDGS (Distiller's Dried Grains with Solubles) instead of the rice bran, the water-soluble protein was prepared as in Example 1 of the present invention. DDGS was obtained by drying the distillation residue generated in the food-based ethanol plant.

The enzymatic degradation reaction was performed as in Example 1 of the present invention. The concentration of the finally obtained glucose (g/L) was measured. The results are shown in FIG. 6.

Example 23

Except for using DWG instead of the rice bran, the water-soluble protein was prepared as in Example 1 of the present invention. DWG was the distillation residue generated in the food-based ethanol plant without being drying.

The enzymatic degradation reaction was performed as in Example 1 of the present invention. The concentration of the finally obtained glucose (g/L) was measured. The results are shown in FIG. 6.

Example 24

Except for using the wheat bran instead of the rice bran, the water-soluble protein was prepared as in Example 1 of the present invention.

The enzymatic degradation reaction was performed as in Example 1 of the present invention. The concentration of the finally obtained glucose (g/L) was measured. The results are shown in FIG. 6.

Example 25

Except for using the starch factory residue instead of the rice bran, the water-soluble protein was prepared as in Example 1 of the present invention.

The enzymatic degradation reaction was performed as in Example 1 of the present invention. The concentration of the finally obtained glucose (g/L) was measured. The results are shown in FIG. 6.

Example 26

Except for using the mixture of yeast and DDGS (yeast: DDGS=50 mass %: 50 mass %) instead of the rice bran, the water-soluble protein was prepared as in Example 1 of the present invention.

The enzymatic degradation reaction was performed as in Example 1 of the present invention. The concentration of the finally obtained glucose (g/L) was measured. The results are shown in FIG. 6.

Based on the results shown in FIG. 6, it was demonstrated that the concentrations of the finally obtained glucose were about 80 g/L in the cases where the water-soluble protein prepared by using the animal proteins and the vegetable proteins derived from the rice bran and other materials as in Example 1, and Examples 20 to 26 of the present invention.

INDUSTRIAL APPLICABILITY

The present invention relates to a method of efficiently producing saccharides having glucose as the major component by inexpensively suppressing the non-productive adsorption of the enzyme to lignin is provided.

The invention claimed is:

1. A method of producing saccharides comprising:
a first step of preparing water-soluble proteins by adding a waste containing at least any one of an animal protein and a vegetable protein to an aqueous sodium hydroxide solution or an aqueous calcium hydroxide solution for the at least any one of the animal protein and the vegetable protein to be converted into the water-soluble proteins;
a second step of adding the water-soluble proteins to a slurry including a biomass; and
a third step of producing saccharides having glucose as a major component by adding a cellulase to the slurry in or after the second step to degrade at least any one of a cellulose or a hemicellulose included in the biomass by the cellulase, wherein
a concentration of the aqueous sodium hydroxide solution or a concentration of the aqueous calcium hydroxide solution is 0.05 mol/L to 1 mol/L,
an addition amount of the at least any one of the animal protein and the vegetable protein with respect to the aqueous sodium hydroxide solution or the aqueous calcium hydroxide solution is 1 mass % to 30 mass % of the aqueous sodium hydroxide solution or the aqueous calcium hydroxide solution,
a temperature of a reaction between: the aqueous sodium hydroxide solution or the aqueous calcium hydroxide solution; and the at least any one of the animal protein and the vegetable protein, in the first step is 50° C. to 160° C., and
the waste is selected from a group consisting of: cell bodies of yeast; cell bodies of filamentous fungi; internal organs of livestock; skins of livestock; a distillation residue generated from a food-based ethanol plant; proteins of cereals generated from the starch factory, the grinding factory, or the rice mill factory; and a mixture thereof.

2. The method of producing saccharides according to claim 1, wherein a time of the reaction between: the aqueous sodium hydroxide solution or the aqueous calcium hydroxide solution; and the at least any one of the animal protein and the vegetable protein, in the first step is 5 minutes to 90 minutes.

3. The method of producing saccharides according to claim 1, wherein a time of the reaction between: the aqueous sodium hydroxide solution or the aqueous calcium hydroxide solution; and the at least any one of the animal protein and the vegetable protein, in the first step is 10 minutes to 60 minutes.

4. The method of producing saccharides according to claim 1, wherein an addition amount of the water-soluble protein with respect to the slurry is 5 mg/g-dry to 40 mg/g-dry per 1 g of the dried biomass.

5. The method of producing saccharides according to claim 1, wherein an addition amount of the water-soluble protein with respect to the slurry is 5 mg/g-dry to 20 mg/g-dry per 1 g of the dried biomass.

6. The method of producing saccharides according to claim 1, wherein
the concentration of the aqueous sodium hydroxide solution or the concentration of the aqueous calcium hydroxide solution is 0.1 mol/L to 0.5 mol/L,
the addition amount of the at least any one of the animal protein and the vegetable protein is 5 mass % to 20 mass %, and
the temperature of the reaction in the first step is 70° C. to 100° C.

7. The method of producing saccharides according to claim 1, wherein the waste is: yeast bodies or a distillation residue generated from a food-based ethanol plant.

* * * * *